United States Patent [19]
Bombardelli et al.

[11] Patent Number: 6,121,277
[45] Date of Patent: Sep. 19, 2000

[54] CAMPTOTHECIN-SKELETON COMPOUNDS ISOLATED FROM *MAPPIA FOETIDA* AND THE USE THEREOF AS SYNTONES FOR NOVEL MEDICAMENTS AS WELL AS THERAPEUTICAL AGENTS

[75] Inventors: Ezio Bombardelli, Milan; Luisella Verotta, Gallarate, both of Italy

[73] Assignee: Indena S.p.A., Milan, Italy

[21] Appl. No.: 09/155,960

[22] PCT Filed: May 2, 1997

[86] PCT No.: PCT/EP97/02244

§ 371 Date: Oct. 6, 1998

§ 102(e) Date: Oct. 6, 1998

[87] PCT Pub. No.: WO97/43290

PCT Pub. Date: Nov. 20, 1997

[30] Foreign Application Priority Data

May 10, 1996 [IT] Italy .................................. MI96A0944

[51] Int. Cl.⁷ ........................ C07D 471/04; A61K 31/437
[52] U.S. Cl. ............................................. 514/284; 546/70
[58] Field of Search ............................... 546/70; 514/284

[56] References Cited

U.S. PATENT DOCUMENTS 5,525,609  6/1996  Bombardelli et al. .................. 514/285

FOREIGN PATENT DOCUMENTS 0 685 481  7/1994  European Pat. Off. .

OTHER PUBLICATIONS

Journal of Medicinal Chemistry, vol. 22, No. 3, 1979, Washington US, pp. 310–314, "Prodrug analogues of the antitumor alkaloid camptothecin".

Primary Examiner—Alan L. Rotman
Attorney, Agent, or Firm—Pennie & Edmonds LLP

[57] ABSTRACT

The present invention relates to camptothecin-skeleton alkaloids isolated from Mappia foetida or obtained by semisynthesis from said alkaloids.

*Mappia foetida*, a plant growing in the Indian subcontinent, is known to contain in its various parts, mainly in the seeds, camptothecin, mappicine and foetidine I and II (EP-A-685481).

The alkaloids of the invention have the following general formula:

(1)

[Chemical structure diagram showing a camptothecin skeleton with substituents R, OR$_2$, COR$_1$, OH]

in which R is a hydrogen atom or a methoxy group; $R_1$ is hydroxy, an OM group wherein M is an alkali cation, preferably sodium or potassium, a $C_1$–$C_6$ alkoxy group, an optionally substituted phenoxy group, an amino, $C_1$–$C_6$ monoalkylamino or $C_2$–$C_{12}$ dialkylamino group in which the alkyl moiety is optionally substituted by amino groups, an arylamino group; $R_2$ is a $C_1$–$C_6$ alkyl group or a group of formula COR$_3$ wherein $R_3$ is alkyl $C_1$–$C_6$ or optionally substituted phenyl or benzyl.

6 Claims, No Drawings

CAMPTOTHECIN-SKELETON COMPOUNDS ISOLATED FROM *MAPPIA FOETIDA* AND THE USE THEREOF AS SYNTONES FOR NOVEL MEDICAMENTS AS WELL AS THERAPEUTICAL AGENTS

TECHNICAL FIELD

The present invention relates to camptothecin-skeleton alkaloids isolated from *Mappia foetida* or obtained by semi-synthesis from said alkaloids.

BACKGROUND ART

*Mappia foetida*, a plant growing in the Indian subcontinent, is known to contain in its various parts, mainly in the seeds, camptothecin, mappicine and foetidine I and II (EP-A-685481). Camptothecin derivatives and their preparation are also described in the Journal of Medicinal Chemistry", Vol. 22, No. 3, 1979.

SUMMARY OF THE INVENTION

The alkaloids of the invention have the following general formula:

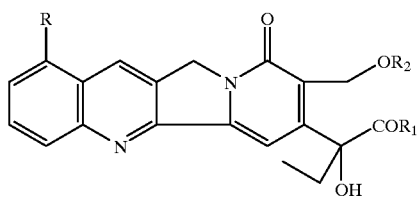

(1)

in which R is a hydrogen atom or a methoxy group; $R_1$ is hydroxy, an OM group wherein M is an alkali cation, preferably sodium or potassium, a $C_1$–$C_6$ alkoxy group, an optionally substituted phenoxy group, an amino, $C_1$–$C_6$ monoalkylamino or $C_2$–$C_{12}$ dialkylamino group in which the alkyl moiety is optionally substituted by amino groups, an arylamino group; $R_2$ is a $C_1$–$C_6$ alkyl group or a group of formula $COR_3$ wherein $R_3$ is alkyl $C_1$–$C_6$ or optionally substituted phenyl or benzyl.

The phenoxy, phenyl or benzyl groups can be substituted by halogen atoms; $C_1$–$C_6$ alkyl, $C_1$–$C_6$ alkoxy, nitro, cyano, $C_1$–$C_3$ haloalkyl groups.

DETAILED DESCRIPTION OF THE INVENTION

The compounds 1 in which R is hydrogen or methoxy, $R_1$ is hydroxy or an OM group (M=sodium or potassium) and $R_2$ is acetyl can be isolated from *Mappia foetida* extracting the artificially dried vegetable biomass at temperatures not higher than 50° C., preferably at 35° C., first with aliphatic ketones or aliphatic esters and subsequently with aliphatic alcohols. In these operative conditions, the 17-acetyl derivatives of camptothecinic and 9-methoxy-camptothecinic acids can be extracted in high yields. Although *Mappia foetida* has been widely studied as a camptothecin selective source, said alkaloids were not identified, due likely to their degradation to camptothecin during the extraction using unsuitable solvents. In the presence of aliphatic alcohols these alkaloids are easily converted into camptothecin even at the extraction natural pH.

The same group of compounds can be obtained by selective acetylation of the $C_{17}$ hydroxyl of camptothecin in alkali medium.

The resulting compounds can in their turn be used as starting materials for the preparation of other compounds of formula 1 in which $R_2$ is different from acetyl and/or $R_1$ is an alkoxy, phenoxy or amino group as defined above or for the preparation of Foetidines I and II. For this purpose, conventional methods for the preparation of esters or amides can be used, for example the reaction of compounds 1 in which $R_1$ is an OM group with alkyl halides such as ethyl or benzyl bromoacetate for the preparation of esters, or the reaction of compounds 1 in which $R_1$ is OH with amine and dicyclohexylcarbodiimide for the preparation of amides.

Compounds 1 have cytotoxic activity against tumor cell lines. For example, Table 1 reports the cytotoxic activity against a colon carcinoma line (HCT116) and against the same line resistant to the most common chemotherapeutics (HCT116/VM46). The results evidenced how a compound of the invention is more active than camptothecin.

TABLE 1

Cytotoxic activity of 17-acetyl-camptothecinic acid and of camptothecin Examples

| | $IC_{50}$ (nMoles/ml) | |
|---|---|---|
| | Line HCT116 | Line HCT116/VM46 |
| Camptothecin | 10.5 | 96.7 |
| 17-Acetyl-camptothecinic acid | 8.2 | 25.3 |

The compounds 1 can therefore be used as active principles in antitumor pharmaceutical compositions in admixture with suitable carriers, for example injectable physiological solutions. The dosages can vary within wide limits (5 to 500 mg/day) but in principle they will be about 10 mg alkaloid a day.

The following examples further illustrate the invention.

Example 1

Isolation of 17-acetyl-camptothecinic and 17-acetyl-9-methoxy camptothecinic acids 3 Kg of *Mappia foetida* seeds were extracted three times with dry acetone (3×3 l) at room temperature. The combined extracts were concentrated to dryness to obtain 580 g of a waxy mass containing camptothecin, 9-methoxy-camptothecin and a small amount of 17-acetyl-camptothecinic acid. The vegetable material from the acetone extraction was re-extracted repeatedly with methanol (3×3 l) at 10° C.; after concentrating the extracts at low temperature, 200 g of a dry residue were obtained, which were suspended in 1 l of water and extracted three times with 500 ml of n-butanol; the combined butanol extracts were concentrated to dryness under vacuum at temperatures not higher than 30° C. 28.9 g of an alkaloid fraction rich in a mixture of 17-acetyl-camptothecinic and 9-methoxy-17-acetyl-camptothecinic acids were obtained and chromatographed in reverse phase through a RP18 column eluting with methanol/water and methanol to obtain three fractions consisting respectively of cumaroylagmatine and camptothecinic acids. This fraction was purified further over silica gel to obtain 3.8 g of 17-acetyl-camptothecinic acid having the following spectroscopical and chemical-physical characteristics: m.p.: 258° C., $\alpha_D$=+63.4 (c=0.05, $H_2O$); $^1H$—NMR (DMSO-$d_6$) δ: 0.85 (t, 3 H, H-18), 1.95 (m+s, 5 H, H-19+ $COCH_3$), 5.20 (s, 2 H, H-17), 5.40,60 (q, $J_{AB}$=10.6 Hz, H-5), 7.65–8.65 (m, 6 H, arom).

The amount of 9-methoxy-17-acetyl-camptothecinic acid is one fifth of the preceding one and has the following chemical-physical characteristics: m.p. 208° C. $\alpha_D$=56.4 (c=0.05 $H_2O$).

Example 2
Preparation of 17-acetyl-camptothecinic acid from camptothecin 1 g of camptothecin was suspended in 30 ml of water, added with 340 mg of NaOH and kept under stirring at 40° C. for two hours or in any case until complete dissolution; water was removed under vacuum and the residue taken up in 20 ml of DMF under strong reaction; the solution was gradually added with 600 mg of acetic anhydride and the whole was kept under stirring for about 2 hours. The solvent was removed under vacuum and the residue was partitioned in a chloroform/methanol/water 5:6:4 mixture. The methanol phase was concentrated to dryness and the residue was crystallized to yield 17-acetyl-camptothecinic acid having the same characteristics as those reported in Example 1.

Example 3
17-Acetylcamptothecin-21-methyl ester

17-Acetylcamptothecin (100 mg, 0.25 mmoles) was dissolved in dry DMF (8 ml) and dry potassium carbonate (68 mg, 0.49 mmoles) and iodomethane (69 mg, 0.49 mmoles) were added thereto, stirring at room temperature for 20 hours. The reaction mixture was filtered and washed with chloroform (5 ml). The filtrates were diluted with chloroform (10 ml) and washed with water (5 ml×3). The organic phase was dried over dry sodium sulfate. After filtration, the solvent was removed under vacuum and the residue (170 mg) was subjected to flash chromatography (CHCl$_3$; CH$_3$OH=9:1). The title compound was obtained (45 mg, yield: 45%) as a solid.

$^1$H NMR (CDCl$_3$) δ: 1.02 (t, J=7 Hz, 3 H, H-18), 2.09 (s, 3 H, OCOCH$_3$), 2.26–2.45 (m, 2 H, H-19), 3.82 (s, 3 H, OCH$_3$), 5.38 (s, 2 H, H-5), 5.52 (s, 2 H, H-17), 7.51–8.42 (m, 6 H, arom)

MS (EI) M$^+$ 422 m.p. (decomp.): 234–235° C.

Following the same process, but using ethyl bromoacetate or t-butyl bromoacetate instead of iodomethane, the corresponding ethyl (a) or t-butyl (b) esters were obtained:

(a) $^1$H NMR (CDCl$_3$) δ: 1.10 (t, J=7.5 Hz, 3 H, H-18), 1.30 (t, J=7.5 Hz, 3 H, CH$_3$), 2.10 (s, 3 H, OCOCH$_3$), 2.30–2.55 (m, 2 H, H-19), 4.25 (q, J=7.5 Hz, 2 H, CH$_2$), 4.70 (q, J$_{AB}$=15 Hz, 2 H, OCOCH$_2$CO), 5.32 (s, 2 H, H-5), 5.52 (s, 2 H, H-17), 7.6 (m, 5 H, arom).

(b) $^1$H NMR (CDCl$_3$) δ: 1.10 (t, J=7.5 Hz, 3 H, H-18), 1.46 (s, 9 H, C(CH$_3$)$_3$), 2.10 (s, 3 H, OCOCH$_3$), 2.35–2.52 (m, 2 H, H-19), 4.60 (q, J$_{AB}$=15 Hz, 2 H, OCOCH$_2$CO), 5.30 (s, 2 H, H-5), 5.52 (s, 2 H, H-17), 7.58–8.38 (m, 6 H, arom).

Example 4
17-Deacetyl-camptothecin acid, 21-ester

Compound b (60 mg, 0.11 mmoles) was dissolved in dry chloroform (2 ml). Iodotrimethylsilan (33 mg, 0.17 mmoles) was added at 0° C. under nitrogen atmosphere, stirring at 0° C. for 1 hour and at room temperature for 1 hour. The reaction mixture was poured into a 5% NaHCO$_3$ solution (5 ml). The aqueous phase was washed repeatedly with chloroform until the chloroform phase became colourless. The aqueous phase was neutralized with a 2.5% HCl solution at 0° C. until pH 7 and extracted with butanol (5 ml×6). The butanol phases were combined and evaporated under vacuum to give a residue (51 mg) which was subjected to flash chromatography through silica gel eluting with chloroform-methanol, to give the title compound (11 mg).

$^1$H NMR (DMSO-d6) δ: (ppm) 0.82 (t, J=7 Hz, 3 H, H-18), 2.12 (s+m, 5 H, H-19 and H-17), 4.29 (f, J$_{AB}$=15 Hz, 2 H, $$\overset{O}{\underset{}{\|}}{C} - O\underline{CH_3}\overset{O}{\underset{}{\|}}{C}),$$

5.22 (s, 2 H, H-5), 6.62 (s, 1 H, OH), 7.50–8.62 (m, 6 H, arom).

$^{13}$C NMR (DMSO-d6) δ: (ppm) 7.7 (t, C-19), 13.7 (t, C-17), 30.01 (f, C-18), 50.2 (f, C-5), 63.9 (f, C-5), 77.5 (s, C-20), 99.1 (d, C-14), 125.9 (s, C-16), 127.3 (d, C-10), 127.8 (s, C-8), 128.6 (d, C-9), 128.9 (d, C-12), 129.7 (s, C-6), 130.3 (d, C-11), 131.4 (d, C-7), 141.3 (s, C-3), 148.0 (s, C-13), 150.7 (s, C-15), 153.9 (s, C-2), 160.8 ( s, 16a), 171.0

$$(s, -\underset{}{\overset{O}{\underset{}{\|}}}\underline{C}OH),$$

172.8 (s, C-21).

What is claimed is:

1. A compound having the formula (1):

(1)

in which R is a hydrogen atom or a methoxy group; R$_1$ is hydroxy, an OM group wherein M is an alkali cation, a C$_1$–C$_6$ alkoxy group, an optionally substituted phenoxy group, an amino, C$_1$–C$_6$ monoalkylamino or C$_2$–C$_{12}$ dialkylamino group in which the alkyl moiety is optionally substituted by amino groups or an arylamino group; R$_2$ is a C$_1$–C$_6$ alkyl group or optionally substituted phenyl or benzyl, with the proviso that R, R$_1$, and R$_2$ are not simultaneously H, NHCH(CH$_3$)$_2$, COCH$_3$/COC$_5$H$_{11}$, resepctively.

2. The compound having the formula (1) according to claim 1, wherein M is an alkali cation selected from the group consisting of sodium and potassium.

3. The compound having the formula (1) according to claims 1–2 wherein R is hydrogen or methoxy, R$_1$ is hydroxy or a OM group and R$_2$ is acetyl.

4. A pharmaceutical composition containing a compound of claim 1 as an active ingredient in an admixture with a pharmaceutically acceptable carrier or diluent.

5. A pharmaceutical composition containing a compound of claim 2 as an active ingredient in an admixture with a pharmaceutically acceptable carrier or diluent.

6. A pharmaceutical composition containing a compound of claim 3 as an active ingredient in an admixture with a pharmaceutically acceptable carrier or diluent.

* * * * *